United States Patent [19]

Berg

[11] Patent Number: 5,094,723

[45] Date of Patent: Mar. 10, 1992

[54] SEPARATION OF M-XYLENE FROM P-XYLENE OR O-XYLENE BY EXTRACTIVE DISTILLATION WITH ALCOHOLS

[75] Inventor: Lloyd Berg, 1314 S. Third Ave., Bozeman, Mont. 59715

[73] Assignee: Lloyd Berg, Bozeman, Mont.

[21] Appl. No.: 635,202

[22] Filed: Jan. 2, 1991

[51] Int. Cl.5 ............................ B01D 3/40; C07C 7/08
[52] U.S. Cl. .................................... 203/56; 203/57; 203/58; 203/60; 203/62; 203/63; 203/64; 203/65; 585/856; 585/860; 585/861; 585/864; 585/865; 585/866
[58] Field of Search ................... 203/56, 63, 64, 60, 203/62, 57, 58, 65; 585/805, 864, 856, 857, 860, 862, 866; 208/313

[56] References Cited

U.S. PATENT DOCUMENTS

| | | | |
|---|---|---|---|
| 2,721,170 | 10/1955 | Johnson | 203/57 |
| 2,849,513 | 8/1958 | Schaeffer | 203/64 |
| 3,089,829 | 5/1963 | Millikan | 203/63 |
| 3,356,593 | 12/1967 | Suzuki | 203/33 |
| 4,488,937 | 12/1984 | Berg et al. | 203/63 |
| 4,676,875 | 6/1987 | Berg et al. | 203/64 |
| 4,822,947 | 4/1989 | Berg et al. | 203/58 |

Primary Examiner—Wilbur Bascomb, Jr.

[57] ABSTRACT m-Xylene is difficult to separate from p-xylene or o-xylene by conventional distillation or rectification because of the close proximity of their boiling points. m-Xylene can be readily separated from p-xylene or o-xylene by using extractive distillation in which the agent is an alcohol. Typical examples of effective agents are: for m-xylene from o-xylene, 1-octanol and cyclododecanol; for p-xylene from m-xylene, diisobutyl carbinol and cyclododecanolphenethyl alcohol mixture.

6 Claims, No Drawings

SEPARATION OF M-XYLENE FROM P-XYLENE OR O-XYLENE BY EXTRACTIVE DISTILLATION WITH ALCOHOLS

FIELD OF THE INVENTION

This invention relates to a method for separating m-xylene from p-xylene or o-xylene using specific alcohols, either alone or admixed with certain organic compounds as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

p-Xylene, B.P.=138.4° C. and m-xylene, B.P.=139.1° C. have a relative volatility of only 1.02 and are virtually impossible to separate by rectification. m-Xylene and o-xylene, B.P.=144.4° C. have a relative volatility of 1.12 and are difficult to separate by rectification. Extractive distillation would be an attractive method of effecting the separation of xylenes if agents can be found that (1) will enhance the relative volatility between the xylenes and (2) are easy to recover from the xylenes, that is, form no azeotrope with xylene and boil sufficiently above xylene to make the separation by rectification possible with only a few theoretical plates.

The advantage of using extractive distillation in this separation can be seen from the data shown in Table 1 below.

TABLE 1

Theoretical and Actual Plates Required vs. Relative Volatility for Xylene Separation

| Relative Volatility | Theoretical Plates Required At Total Reflux; 95% Purity | Actual Plates Required, 75% Eff. |
| --- | --- | --- |
| 1.12 | 52 | 70 |
| 1.20 | 33 | 44 |
| 1.25 | 27 | 36 |
| 1.30 | 23 | 31 |
| 1.35 | 20 | 27 |
| 1.40 | 18 | 24 |
| 1.50 | 15 | 20 |

The relative volatility of m-xylene to o-xylene is 1.12 and thus require 52 theoretical plates for separation by conventional rectification at total reflux. Plates possessing an efficiency of 75% are commonly employed and thus about 70 actual plates are required, clearly a difficult separation. Several of the agents that I have discovered yield a relative volatility of 1.50 which would reduce the plate requirement to only 20.

The relative volatility of p-xylene to m-xylene is only 1.02 making this separation impossible by rectification. If an extractive distillation agent can be found that would increase the relative volatility to 1.2, p-xylene could be separated from m-xylene by rectification in a column with only 44 actual plates.

Extractive distillation typically requires the addition of an equal amount to twice as much extractive agent as the m-xylene and o-xylene on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with o-xylene otherwise it will form a two-phase azeotrope with the o-xylene in the recovery column and some other method of separation will have to be employed.

Previous work on the separation of m-xylene from o-xylene by extractive distillation has been reported by Berg et al. U.S. Pat. No. 4,488,937 described the use of sulfolane; U.S. Pat. No. 4,585,526 used ether-alcohols; U.S. Pat. No. 4,673,465 employed polychloro compounds; U.S. Pat. No. 4,676,872 described adiponitrile; U.S. Pat. No. 4,676,875 reported dimethylformamide and U.S. Pat. No. 4,738,755 used benzoates. None of the agents described in the above five patents were effective in enhancing the relative volatility of p-xylene from m-xylene.

OBJECTIVE OF THE INVENTION

The objects of this invention are to provide a process or method of extractive distillation that will enhance the relative volatility of p-xylene to m-xylene and m-xylene to o-xylene in their separation in a rectification column. It is a further object of this invention to identify compounds that are stable, can be separated from xylenes by rectification with relative few plates and can be recycled to the extractive distillation column with little decomposition.

SUMMARY OF THE INVENTION

The objects of the invention are provided by a process for the separation of m-xylene from o-xylene and p-xylene from m-xylene which entails the use of certain alcohols, either alone or admixed with specific organic compounds as the agent in extractive distillation.

DETAILED DESCRIPTION OF THE INVENTION

I have discovered that certain alcohols, either alone or admixed with other specific organic compounds, will effectively increase the relative volatility between m-xylene and o-xylene or p-xylene from m-xylene and permit the separation of m-xylene from o-xylene or p-xylene from m-xylene when employed as the agent in extractive distillation. Table 2 lists the agents that I have found to be effective in the separation of m-xylene from o-xylene. The data in Table 2 was obtained in a vapor-liquid equilibrium still. The alcohols which are effective are, 1-decanol, diisobutyl carbinol, 1-octanol, 2-octanol, 1-nonanol, undecyl alcohol, isodecanol, isooctanol, isononyl alcohol 1-dodecanol and cyclododecanol. Table 2 also lists a number of non-alcoholic compounds which when mixed with cyclododecanol, gave effective relative volatilities but when used alone, were relatively ineffective. They are dimethylsulfoxide, methyl salicylate, ethyl salicylate, sulfolane, dimethylformamide, dimethylacetamide, acetophenone, nitrobenzene, diethylene glycol butyl ether, diethylene glycol ethyl ether and phenyl acetate. Table 3 lists a number of compounds which might be expected to be effective but were not either when used alone or when mixed with an effective alcohol.

Table 3 lists a number of compounds which might have been expected to act favorably with cyclododecanol in the separation of m-xylene from o-xylene but which failed to yield an effective relative volatility.

Pure cyclododecanol, whose relative volatility had been determined in the vapor-liquid equilibrium still was then evaluated in a glass perforated plate rectification column possessing 7.3 theoretical plates in the extractive distillation mode. It yielded a relative volatility of 1.31 after one hour and 1.37 after two hours of continuous operation. These data are listed in Table 4.

TABLE 2

Effective Agents For Separating m-Xylene From o-Xylene

| Compounds | Relative Volatility |
|---|---|
| Isodecanol (EXXON) | 1.18 |
| 1-Decanol | 1.21 |
| Diisobutyl carbinol | 1.27 |
| 1-Octanol | 1.38 |
| 2-Octanol | 1.30 |
| 1-Nonanol | 1.32 |
| Undecyl alcohol | 1.40 |
| Isodecanol (ASHLAND) | 1.27 |
| Isooctanol (U.C.) | 1.27 |
| Isooctanol (EXXON) | 1.24 |
| Isononyl alcohol (EXXON) | 1.22 |
| 1-Dodecanol | 1.31 |
| Cyclododecanol | 1.37 |
| Cyclododecanol, Dimethylsulfoxide | 1.32 |
| Cyclododecanol, Methyl salicylate | 1.45 |
| Cyclododecanol, Ethyl salicylate | 1.30 |
| Cyclododecanol, Dimethylformamide | 1.34 |
| Cyclododecanol, Sulfolane | 1.38 |
| Cyclododecanol, Acetophenone | 1.31 |
| Cyclododecanol, Dimethylacetamide | 1.35 |
| Cyclododecanol, Nitrobenzene | 1.33 |
| Cyclododecanol, Diethylene glycol butyl ether | 1.42 |
| Cyclododecanol, Diethylene glycol ethyl ether | 1.36 |
| Cyclododecanol, Phenyl acetate | 1.33 |
| Cyclododecanol, Benzyl alcohol | 1.30 |
| Cyclododecanol, 1-Decanol | 1.37 |
| Cyclododecanol, 1-Octanol | 1.36 |
| Cyclododecanol, Isodecanol (EXXON) | 1.46 |
| Cyclododecanol, 2-Octanol | 1.39 |
| Cyclododecanol, Diisobutyl carbinol | 1.40 |
| Tridecyl alcohol | 1.21 |
| Tridecanol | 1.25 |

TABLE 3

Ineffective Agents For Separating m-Xylene From o-Xylene When Mixed With Cyclododecanol

| Compounds | Relative Volatility |
|---|---|
| Methyl benzoate | 1.0 |
| Benzonitrile | 1.16 |
| Butyl butyrate | 1.26 |
| Diethyl malonate | 1.23 |
| Propylene carbonate | 1.07 |
| Adiponitrile | 1.21 |
| 2-Hydroxyacetophenone | 1.21 |
| 2-Ethyl hexyl acetate | 1.22 |
| Benzyl benzoate | 1.0 |
| Diethylene glycol hexyl ether | 0.7 |
| 2-Nitrotouene | 1.25 |
| Diethylene glycol diethyl ether | 1.24 |
| Ethylene glycol butyl ether acetate | 1.1 |
| Propiophenone | 0.8 |
| Phenethyl alcohol | 1.29 |
| 2-Ethyl-1-hexanol | 1.29 |
| Tridecyl alcohol | 1.21 |

TABLE 4

Data From Run Made In Rectification Column - m-Xylene From o-Xylene

| Agent | Column | Time hrs. | Weight % m-Xylene | Weight % o-Xylene | Relative Volatility |
|---|---|---|---|---|---|
| Cyclododecanol | Overhead | 1 | 95.5 | 4.5 | 1.31 |
|  | Bottoms |  | 75 | 25 |  |
| " | Overhead | 2 | 96.5 | 3.5 | 1.37 |
|  | Bottoms |  | 73.6 | 26.4 |  |

Table 5 lists the agents that I have found to be effective in the separation of p-xylene from m-xylene. The data in Table 5 was obtained in a vapor-liquid equilibrium still. The alcohols which are effective in bringing m-xylene out as the overhead from p-xylene are benzyl alcohol, diisobutyl carbinal, 1-dodecanol, 1-nonanol, undecyl alcohol, 1-decanol, isodecanol, tridecanol and tridecyl alcohol. Cyclododecanol brings out the p-xylene as overhead product. The compounds which when mixed with cyclododecanol enhance the relative volatility are benzonitrile, dimethylsulfoxide, dimethylacetamide, dimethylformamide, adiponitrile, diethylene glycol butyl ether, diethylene glycol diethyl ether, butoxypropanol, ethylene glycol butyl ether acetate, phenethyl alcohol, n-octanol, tetrahydrofurfuryl alcohol, propiophenone, benzyl alcohol, isodecyl alcohol and diisobutyl carbinol.

Table 6 lists a number of compounds which might have been expected to to act favorably as agents in the separation of p-xylene from m-xylene but which failed to yield an effective relative volatility.

A mixture comprising 75% cyclododecanol and 25% phenethyl alcohol, whose relative volatility had been determined in the vapor-liquid equilibrium still, was then evaluated in a glass perforated plate rectification column possessing 7.3 theoretical plates in the extractive distillation mode. It yielded a relative volatility of 1.28 after one hour and 1.33 after two hours of continuous operation. These data are listed in Table 7.

TABLE 5

Effective Agents For Separating p-Xylene From m-Xylene

| Compounds | Relative Volatility |
|---|---|
| Cyclododecanol, alone | 1.11 |
| Cyclododecanol, Benzonitrile | 1.16 |
| Cyclododecanol, Dimethylsulfoxide | 1.14 |
| Cyclododecanol, Dimethylacetamide | 1.24 |
| Cyclododecanol, Dimethylformamide | 1.17 |
| Cyclododecanol, Adiponitrile | 1.13 |
| Cyclododecanol, Diethylene glycol butyl ether | 1.16 |
| Cyclododecanol, Diethylene glycol diethyl ether | 1.41 |
| Cyclododecanol, Butoxypropanol | 1.38* |
| Cyclododecanol, Ethylene glycol butyl ether acetate | 1.5* |
| Cyclododecanol, Phenethyl alcohol | 1.35 |
| Cyclododecanol, n-Octanol | 2.3 |
| Cyclododecanol, Tetrahydro furfuryl alcohol | 2.1* |
| Cyclododecanol, Propiophenone | 1.20 |
| Cyclododecanol, Benzyl alcohol | 1.57 |
| Cyclododecanol, Isodecanol (EXXON) | 1.63* |
| Cyclododecanol, Diisobutyl carbinol | 1.73* |
| Benzyl alcohol | 1.19* |
| Isodecanol (EXXON) | 1.21* |
| Diisobutyl carbinol | 1.23* |
| 1-Dodecanol | 1.11* |
| 1-Nonanol | 1.14* |
| Undecyl alcohol | 1.14* |
| 1-Decanol | 1.21* |
| Isodecanol | 1.16* |
| Tridecanol | 1.30* |
| Tridecyl alcohol | 1.25* |

*Brings the m-Xylene out as overhead

TABLE 6

Ineffective Agents For Separating p-Xylene From m-Xylene

| | |
|---|---|
| Butyl benzoate | Benzyl benzoate |
| Butyl butyrate | Nitrobenzene |
| Methyl salicylate | Diethylene glycol hexyl ether |
| Propylene carbonate | Diethylene glycol ethyl ether |
| Diethyl malonate | Butoxypropanol |
| Sulfolane | Phenyl acetate |
| Acetophenone | 2-Octanol |
| 2-Hydroxyacetophenone | 1-Octanol |
| 2-Ethyl hexyl acetate | Tetrahydrofurfuryl alcohol |
| Isooctyl alcohol | Isononyl alcohol |
| 2-Ethyl-1-hexanol | |

TABLE 7

Data From Run Made In Rectification Column - p-Xylene From m-Xylene

| Agent | Column | Time hrs. | Weight % p-Xyene | Weight % m-Xylene | Relative Volatility |
|---|---|---|---|---|---|
| 75% Cyclododecanol, | Overhead | 1 | 93.8 | 6.2 | 1.28 |
| 25% Phenethyl alcohol | Bottoms | | 70.8 | 29.2 | |
| 75% Cyclododecanol, | Overhead | 2 | 97.5 | 2.5 | 1.33 |
| 25% Phenethyl alcohol | Bottom | | 68.4 | 31.6 | |

THE USEFULNESS OF THE INVENTION

The usefulness of this invention can be demonstrated by referring to the data presented in Tables 2 to 7. All of the successful agents show that m-xylene can be separated from m-xylene or p-xylene by means of extractive distillation in a rectification column and that the ease of separation as measured by relative volatility is considerable.

WORKING EXAMPLES

Example 1

Ten grams of m-xylene, 30 grams of o-xylene and 20 grams of cyclododecanol were charged to a vapor-liquid equilibrium still and refluxed for three hours. Analysis indicated a vapor composition of 29.8% m-xylene, 70.2% o-xylene; a liquid composition of 23.6% m-xylene, 76.4% o-xylene which is a relative volatility of 1.37.

Example 2

Ten grams of m-xylene, 30 grams of o-xylene, 20 grams of cyclododecanol and ten grams of diisobutyl carbinol were charged to the vapor-liquid equilibrium still and refluxed for 14 hours. Analysis indicated a vapor composition of 31.2% m-xylene, 68.8% o-xylene; a liquid composition of 24.5% m-xylene, 74.5% o-xylene which is a relative volatility of 1.40.

Example 3

225 grams of m-xylene and 75 grams of o-xylene were placed in the stillpot of a glass perforated plate rectification column containing 7.3 theoretical plates, and heated. When refluxing began, an extractive agent comprising cyclododecanol was pumped into the column at a rate of 15 ml/min. The temperature of the extractive agent as it entered the column was 95° C. After establishing the feed rate of the extractive agent, the heat input to the column was adjusted to give a total reflux rate of 40 ml/min. After one hour of operation, overhead and bottoms samples of approximately two ml. were collected and analysed by gas chromatography. The overhead analysis was 95.5% m-xylene, 4.5% o-xylene and the bottoms analysis was 75% m-xylene, 25% o-xylene. Using these compositions in the Fenske equation, with the number of theoretical plates in the column being 7.3, gave an average relative volatility of 1.31 for each theoretical plate. After a total of two hours of continuous operation, samples of overhead and bottoms were again taken and analysed. The overhead analysis was 96.5% m-xylene, 3.5% o-xylene; the bottoms analysis was 73.6% m-xylene, 26.4% o-xylene which is a relative volatility of 1.37. These data are listed in Table 4.

Example 4

Twenty grams of m-xylene, 60 grams of p-xylene, 30 grams of cyclododecanol and 15 grams of benzyl alcohol were charged to the vapor-liquid equilibrium still and refluxed for five hours. Analysis indicated a vapor composition of 86.9% p-xylene, 13.1% m-xylene; a liquid composition of 80.8% p-xylene, 19.2% m-xylene which is a relative volatility of p-xylene to m-xylene of 1.57.

Example 5

Twenty grams of m-xylene, 60 grams of p-xylene, 30 grams of cyclododecanol and 15 grams of diisobutyl carbinol were charged to the vapor-liquid equilibrium still and refluxed for four hours. Analysis indicated a vapor composition of 68.9% p-xylene, 31.1% m-xylene; a liquid composition of 79.3% p-xylene, 20.7% m-xylene which is a relative volatility of m-xylene to p-xylene of 1.73.

Example 6

A glass perforated plate rectification column was calibrated with m-xylene and o-xylene which possesses a relative volatility of 1.11 and found to have 7.3 theoretical plates. A solution comprising 225 grams of p-xylene and 75 grams of m-xylene was placed in the stillpot and heated. When refluxing began, an extractive agent comprising 75% cyclododecanol and 25% phenethyl alcohol was pumped into the column at a rate of 15 ml/min. The temperature of the extractive agent as it entered the column was 95° C. After establishing the feed rate of the extractive agent, the heat input to the p-xylene-o-xylene in the stillpot was adjusted to give a total reflux rate of 40 ml/min. After one hour of operation, the overhead and bottoms samples of approximately two ml. were collected and analysed by gas chromatography. The overhead analysis was 93.8% p-xylene, 6.2% m-xylene and the bottoms analysis was 70.8% p-xylene, 29.2% m-xylene. Using these compositions in the Fenske equation, with the number of theoretical plates in the column being 7.3, gave an average relative volatility of 1.28 for each theoretical plate. After two hours of continuous operation, samples of overhead and bottoms were again taken and analysed. The overhead analysis was 97.5% p-xylene, 2.5% m-xylene; the bottoms analysis was 68.4% p-xylene, 31.6% m-xylene which is a relative volatility of 1.33. These data are listed in Table 7.

I claim:

1. A method for recovering m-xylene from a mixture of m-xylene and o-xylene which comprises distilling a mixture of m-xylene and o-xylene in the presence of about one part of an extractive agent per part of m-xylene-o-xylene mixture, recovering the m-xylene as overhead product and obtaining the o-xylene and the extractive agent from the stillpot, wherein said extractive agent comprises an alcohol selected from the group consisting of 1-decanol, diisobutyl carbinol, 1-octanol, 2-octanol, 1-nonanol, undecyl alcohol, isodecanol, isoctyl alcohol, isononyl alcohol, 1-dodecanol, tridecyl alcohol and cyclododecanol.

2. A method for recovering m-xylene from a mixture of m-xylene and o-xylene which comprises distilling a mixture of m-xylene and o-xylene in the presence of about one part of an extractive agent per part of m-xylene-o-xylene mixture, recovering the m-xylene as overhead product and obtaining the o-xylene and the extractive agent from the stillpot, wherein said extractive agent comprises cyclododecanol and at least one material selected from the group comprising dimethylsulfoxide, dimethylformamide, methyl salicylate, sulfolane, acetophenone, nitrobenzene, diethylene glycol butyl ether, diethylene glycol ethyl ether, phenyl acetate, benzyl alcohol, n-decanol, isodecanol, 2-octanol and diisobutyl carbinol.

3. A method for recovering p-xylene from a mixture of p-xylene and m-xylene which comprises distilling a mixture of p-xylene and m-xylene in the presence of about one part of an extractive agent per part of p-xylene-m-xylene mixture, recovering the p-xylene as overhead product and obtaining the m-xylene and the extractive agent from the stillpot, wherein said extractive agent comprises cyclododecanol and at least one material selected from the group consisting of adiponitrile, benzonitrile, dimethylsulfoxide, dimethylformamide, dimethylacetamide, diethylene glycol butyl ether, diethylene glycol diethyl ether, phenethyl alcohol, n-octanol, propiophenone and benzyl alcohol.

4. A method for recovering m-xylene from a mixture of m-xylene and p-xylene which comprises distilling a mixture of m-xylene and p-xylene in the presence of about one part of an extractive agent per part of m-xylene-p-xylene mixture, recovering the m-xylene as ovehead product and obtaining the p-xylene and the extractive agent from the stillpot, wherein said extractive agent comprises cyclododecanol and at least one material selected from the group consisting of butoxypropanol, ethylene glycol butyl ether acetate and diisobutyl carbinol.

5. A method for recovering p-xylene from a mixture of p-xylene and m-xylene which comprises distilling a mixture of p-xylene and m-xylene in the presence of about one part of an extractive agent per part of p-xylene-m-xylene mixture, recovering the p-xylene as overhead product and obtaining the m-xylene and the extractive agent from the stillpot, wherein said extractive agent comprises cyclododecanol.

6. A method for recovering m-xylene from a mixture of m-xylene and p-xylene which comprises distilling a mixture of m-xylene and p-xylene in the presence of about one part of an extractive agent per part of m-xylene-p-xylene mixture, recovering the m-xylene as overhead product and obtaining the p-xylene and the extractive agent from the stillpot, wherein said extractive agent comprises cyclododecanol and at least one material selected from the group consisting of isodecanol, butoxypropanol, ethylene glycol butyl ether acetate and diisobutyl carbinol, Action on the merits of this amendment is solicited.

* * * * *